US008898830B2

(12) United States Patent
Hushek

(10) Patent No.: US 8,898,830 B2
(45) Date of Patent: *Dec. 2, 2014

(54) PATIENT SUPPORT AND TRANSPORT SYSTEM OF A MULTIMODALITY MEDICAL SUITE

(71) Applicant: MedTrak Holding Company, LLC, Wauwatosa, WI (US)

(72) Inventor: Stephen G. Hushek, Wauwatosa, WI (US)

(73) Assignee: Medtrak Holding Company, LLC, Wauwatosa, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/019,732

(22) Filed: Sep. 6, 2013

(65) Prior Publication Data

US 2014/0000025 A1 Jan. 2, 2014

Related U.S. Application Data

(63) Continuation-in-part of application No. 13/225,646, filed on Sep. 6, 2011, now Pat. No. 8,584,274, and a continuation-in-part of application No. 13/092,643, filed on Apr. 22, 2011, now Pat. No. 8,555,578.

(51) Int. Cl.
*A61G 7/10* (2006.01)
*A61G 7/08* (2006.01)
*A61M 16/01* (2006.01)
*A61G 12/00* (2006.01)

(52) U.S. Cl.
CPC ............... *A61G 7/08* (2013.01); *A61G 7/1019* (2013.01); *A61G 7/103* (2013.01); *A61G 7/1042* (2013.01); *A61M 16/01* (2013.01); *A61G 12/008* (2013.01); *A61G 12/004* (2013.01); *A61G 2210/50* (2013.01); *A61G 12/005* (2013.01); *A61G 12/007* (2013.01)
USPC ..................... 5/86.1; 5/81.1 R; 5/85.1; 5/87.1

(58) Field of Classification Search
CPC . A61G 7/1046; A61G 7/1017; A61G 7/1057; A61G 7/1042; A61G 7/1055; A61G 13/00; A61G 7/008; A61G 7/1013; A61G 12/004; A61B 6/04; A61B 6/0457; A61B 6/0407; A61B 6/0442; A61B 6/5247
USPC ........... 5/81.1 R, 83.1, 85.1, 87.1, 84.1, 89.1, 5/86.1
See application file for complete search history.

(56) References Cited

U.S. PATENT DOCUMENTS 4,243,147 A * 1/1981 Twitchell et al. ............. 212/284
4,738,369 A 4/1988 Desjardins (Continued)

FOREIGN PATENT DOCUMENTS

WO 2009036174 3/2009

*Primary Examiner* — Robert G Santos
*Assistant Examiner* — Richard G Davis
(74) *Attorney, Agent, or Firm* — Reinhart Boerner Van Deuren s.c.

(57) ABSTRACT

A patient support and transport system for a multi-modality medical suite includes a track system with one track in one room aligned with another track in another room. A support carriage coupled to the track system and configured to move between the two rooms. A duplex socket interface module attached to the support carriage and flexible raceway including a first conduit management system coupled to the support carriage and configured to automatically couple with and decouple with the duplex socket interface module. A second conduit management system is coupled to electrical and data ports and include a conduit interface module configured to automatically couple with and decouple with the duplex socket interface module. The patient support and transport system also includes a vertical support member coupled to the support carriage and a support assembly coupled to the vertical support member configured to selectively articulate a patient bed.

15 Claims, 14 Drawing Sheets

(56) References Cited

U.S. PATENT DOCUMENTS

| | | | | |
|---|---|---|---|---|
| 5,158,188 A | * | 10/1992 | Nordberg | 212/312 |
| 5,259,011 A | * | 11/1993 | Petro | 378/4 |
| 5,456,655 A | * | 10/1995 | Morris | 601/23 |
| 5,490,297 A | | 2/1996 | Bradcovich et al. | |
| 5,570,483 A | | 11/1996 | Williamson | |
| 5,611,638 A | | 3/1997 | Dorr et al. | |
| 5,618,090 A | | 4/1997 | Montague et al. | |
| 5,651,150 A | | 7/1997 | Kanitzer et al. | |
| 5,730,410 A | | 3/1998 | Archambault et al. | |
| 5,749,374 A | | 5/1998 | Schneider, Sr. | |
| 5,939,857 A | * | 8/1999 | Madigan et al. | 320/107 |
| 6,089,518 A | | 7/2000 | Nilsson | |
| 6,179,260 B1 | | 1/2001 | Ohanian | |
| 6,195,578 B1 | | 2/2001 | Distler et al. | |
| 6,523,195 B1 | | 2/2003 | Rodier et al. | |
| 6,640,364 B1 | | 11/2003 | Josephson et al. | |
| 6,708,622 B2 | * | 3/2004 | Bergeron | 104/96 |
| 6,711,759 B1 | | 3/2004 | Kluckhuhn | |
| 6,782,571 B1 | | 8/2004 | Josephson et al. | |
| 6,845,533 B1 | | 1/2005 | Tulette | |
| 6,854,140 B2 | | 2/2005 | Bartels et al. | |
| 6,928,672 B2 | | 8/2005 | Pastyr et al. | |
| 6,971,126 B1 | | 12/2005 | Kluckhuhn | |
| 7,190,991 B2 | * | 3/2007 | Cable et al. | 600/407 |
| 7,237,491 B2 | * | 7/2007 | Faucher et al. | 104/89 |
| 7,303,049 B1 | * | 12/2007 | Greenlee | 182/37 |
| 7,578,241 B2 | | 8/2009 | Hjort | |
| 7,818,838 B2 | | 10/2010 | Erbel et al. | |
| 7,930,775 B2 | | 4/2011 | Kluckhuhn | |
| 8,073,524 B2 | * | 12/2011 | Saunders et al. | 600/410 |
| 8,190,235 B2 | | 5/2012 | Scarth et al. | |
| 8,295,905 B2 | | 10/2012 | Graves et al. | |
| 8,598,554 B2 | | 12/2013 | Rees | |
| 2004/0102690 A1 | * | 5/2004 | Bartels et al. | 600/407 |
| 2006/0236456 A1 | | 10/2006 | Beale | |
| 2006/0260050 A1 | * | 11/2006 | Manzione | 5/601 |
| 2007/0238950 A1 | | 10/2007 | Vija et al. | |
| 2008/0281181 A1 | * | 11/2008 | Manzione et al. | 600/407 |
| 2009/0124884 A1 | * | 5/2009 | Saunders et al. | 600/410 |
| 2009/0217456 A1 | | 9/2009 | Lempen et al. | |
| 2010/0031443 A1 | * | 2/2010 | Georgiev et al. | 5/601 |
| 2010/0107320 A1 | * | 5/2010 | Rees | 2/456 |
| 2010/0138997 A1 | | 6/2010 | Hoppner et al. | |

* cited by examiner

PATIENT SUPPORT AND TRANSPORT SYSTEM OF A MULTIMODALITY MEDICAL SUITE

This patent application is a continuation-in-part of and claims priority to application Ser. No. 13/225,646, filed Sep. 6, 2011, entitled "Patient Support and Transport System;" which is a continuation-in-part of application Ser. No. 13/092,643, filed on Apr. 22, 2011, entitled "Shielded Movable Door Element of a Multimodality Medical Suite," both of which are incorporated herein, in their entirety, by this reference.

BACKGROUND OF THE INVENTION

Field of the Invention

The present disclosure is directed to medical equipment and more particularly to a patient transport apparatus movable between a first room and a second room of a multimodality medical suite.

Operating rooms will often feature sophisticated imaging systems such as magnetic resonance scanners, computed tomography scanners, or angiography systems to provide a physician with sub-surface visualization capabilities of the patient. Such equipment allows the physician to select an incision site more precisely and reduce the size of an incision during surgery or precisely target the anatomy of interest during a stereotactic procedure. The difficulties associated with locating these imaging systems in an operating room have led vendors to implement multi-room suites with patient transport systems to move the patient from the surgical/procedural/treatment environment to an imaging environment.

Of particular concern is when a patient is under anesthesia because of a risk associated with dislocation of the airway or the multitude of intravenous fluid lines and other invasive devices associated with anesthesia and patient monitoring. The anesthesiologist and their assistants are forced to walk alongside the patient during transport, manually rolling the anesthesia machine and patient monitoring system alongside the patient. Such personnel ensure that none of the tubes, or lines, or hoses get pulled or experience significant tension, while the gas lines, power cords, and data lines stretch progressively further from their connection points. Such situation also creates a trip and disconnect hazard. In some cases, the anesthesiologists are forced to disconnect the anesthesia machine from the gas ports in one room and reconnect them to different ports in the second room. During the transition or movement of the patient from one room to another an anesthesiologist, or an assistant, has to "bag" the patient. If multiple room-to-room transitions are required, the anesthesia disconnects and reconnects are, at the least, inconvenient and potentially dangerous.

An additional problem occurs when moving a patient into a magnetic resonance imaging (MRI) room because the radio frequency (RF) shielding doors must provide a complete seal to prevent electronic noise from getting into the MR room and corrupting the images. Thus, the doors must provide the seal when a diagnostic patient is being scanned and the anesthesia connections are not coming into the room, as well as when a surgical patient is being scanned and the anesthesia connections are coming into the room.

The apparatus of the present disclosure must also be of construction which is both durable and long lasting, and it should also require little or no maintenance to be provided by the user throughout its operating lifetime. In order to enhance the market appeal of the apparatus of the present disclosure, it should also be of inexpensive construction to thereby afford it the broadest possible market. Finally, it is also an objective that all of the aforesaid advantages and objectives be achieved without incurring any substantial relative disadvantage.

SUMMARY OF THE INVENTION

The disadvantages and limitations of the background art discussed above are overcome by the present disclosure.

There is provided a patient support and transport system for a multi-modality medical suite including at least two clinical treatment rooms separated by a wall including a moveable door. At least one room is configured with an imaging system.

The patient support and transport system includes a track system comprising a pair of tracks, with one track in one room aligned with another track in the other room. A support carriage is coupled to the track system and configured to move between the two rooms of the suite. A flexible raceway is configured to extend within the length of the two rooms of the suite, with one end of the raceway coupled to a duplex socket interface module coupled to the support carriage. The vertical support member is coupled to the support carriage. A support assembly is removably coupled to the vertical support member and configured to one of selectively articulate a patient bed attached to the patient bed and selectively decouple the patient bed and position the patient bed on a platform associated with the imaging system.

In another embodiment, the patient support and transport system for a multi-modality medical suite further includes a motor controller coupled to a motor in the support carriage and configured to control movement of the carriage in a smooth motion from one room to another room of the suite.

In another embodiment, the patient support and transport system for a multi-modality medical suite provides that the flexible raceway includes a first conduit management system and a second conduit management system. The first conduit management system includes a first conduit interface module configured to automatically couple with and decouple from the duplex socket interface module, with the first conduit management system coupled to electrical and data ports in the medical treatment room.

The second conduit management system is coupled to electrical and data ports in the room with the imaging system and includes a second conduit interface module configured to automatically couple with and decouple from the duplex socket interface module upon movement of the support carriage respectively into and out of the room with the imaging system.

There is further provided a patient support and transport system for a multi-modality medical suite including at least two clinical treatment rooms separated by a wall including a moveable door. At least one room is configured with an imaging system.

The patient support and transport system includes a track system comprising a pair of tracks, with one track in one room aligned with another track in the other room. A support carriage is coupled to the track system and configured to move between the two rooms of the suite. A duplex socket interface module is attached to the support carriage.

There is also included a flexible raceway including a first conduit management system and a second conduit management system. The first conduit management system includes a first conduit interface module configured to automatically couple with and decouple from the duplex socket interface module, with the first conduit management system coupled to electrical and data ports in the medical treatment room.

The second conduit management system is coupled to electrical and data ports in the room with the imaging system and includes a second conduit interface module configured to automatically couple with and decouple from the duplex socket interface module upon movement of the support carriage respectively into and out of the room with the imaging system. The patient support and transport system for a multi-modality medical suite also includes a vertical support member coupled to the support carriage and a support assembly coupled to the vertical support member and configured to selectively articulate a patient bed attached to the support assembly.

Another embodiment of the patient support and transport system for a multi-modality medical suite provides the support assembly is coupled to the vertical support member in a cantilevered aspect at one end of the support assembly and configured to position a portion of the patient bed at the isocenter of the imaging system.

There is further provided a patient support and transport system for a multi-modality medical suite including at least two clinical treatment rooms separated by a wall including a door. One room is configured with an imaging system.

The patient support and transport system includes a track system comprising a pair of tracks with one track in one room aligned with another track in another room. A support carriage is coupled to the track system and configured to move between two rooms of the suite.

A flexible raceway is configured to extend within the length of the two rooms of the suite with one end of the raceway coupled to the support carriage with the flexible raceway further configured to selectively extend through a moveable door element in the door of the wall of the modality medical suite. The door is part of the wall positioned between the rooms of the suite.

The moveable door element includes a housing coupled to the door and configured to selectively move from a first position to a second position. The housing is further configured to move to the second position when a shield door component, coupled to the raceway, replaces the housing and is disposed in a space in the portion of the door vacated by the door element. A moveable door element further includes a shield component disposed in the housing. The patient support and transport system for a multi-modality medical suite also includes a vertical support member coupled to the support carriage and a support assembly coupled to the vertical support member and configured to selectively articulate a patient bed attached to the support assembly.

The apparatus of the present disclosure is of a construction which is both durable and long lasting, and which will require little or no maintenance to be provided by the user throughout its operating lifetime. The apparatus of the present disclosure is also of inexpensive construction to enhance its market appeal and to thereby afford it the broadest possible market. Finally, all of the aforesaid advantages and objectives are achieved without incurring any substantial relative disadvantage.

DESCRIPTION OF THE DRAWINGS

These and other advantages of the present disclosure are best understood with reference to the drawings, in which.

DETAILED DESCRIPTION OF THE EXEMPLARY EMBODIMENTS

Figure 1:
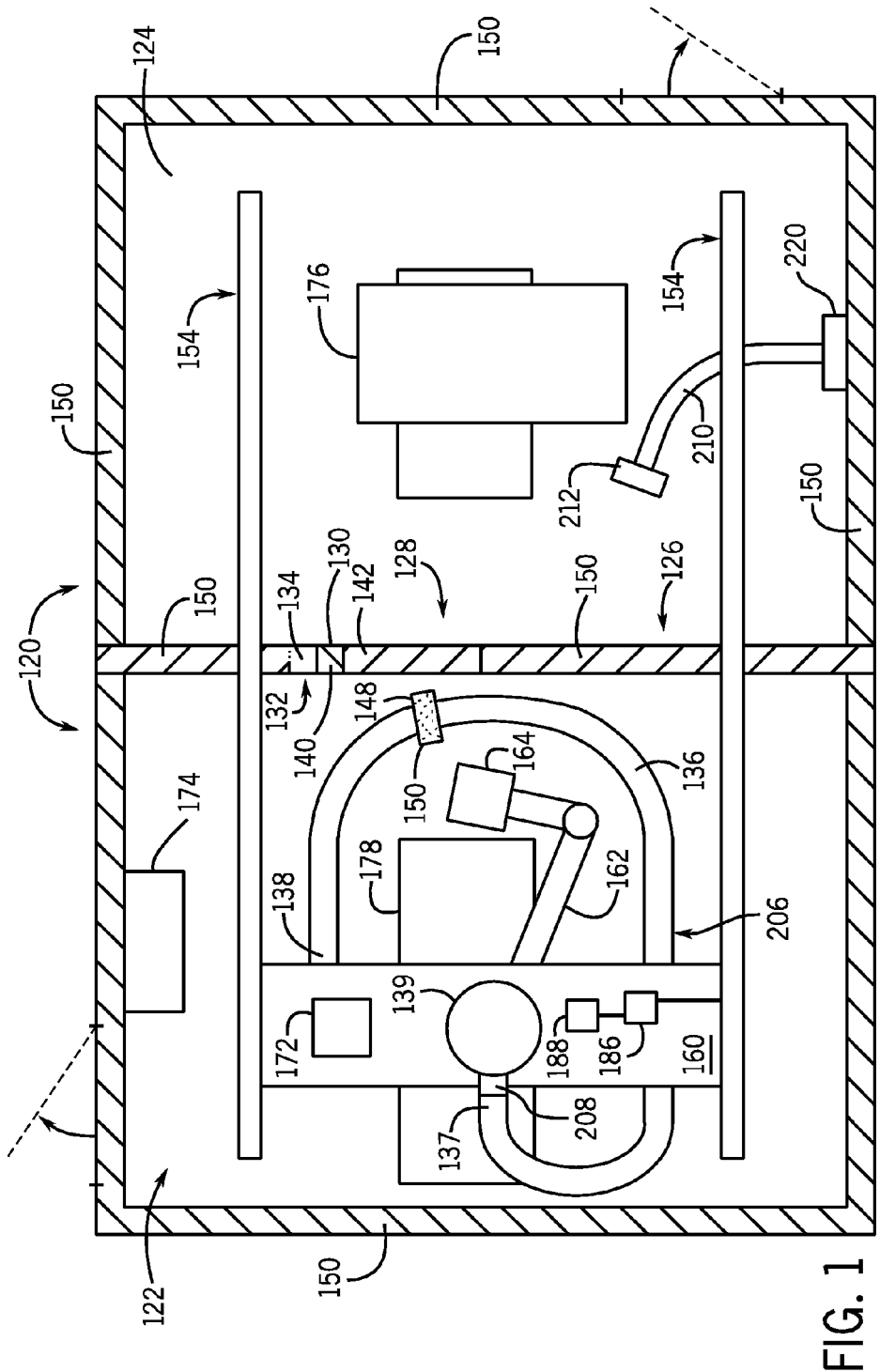
FIG. 1 is a schematic, top view of an exemplary embodiment of a multimodality medical suite, including a patient transport apparatus, track system, cable/hose management system and supporting carriage, with a wall having a door apparatus including a movable door element.

Referring to the Figures, FIG. 1 illustrates a schematic, top view of an exemplary embodiment of a multimodality medical suite 120. The multimodality medical suite 120 includes a first room 122 and a second room 124 separated by a wall 126. The multimodality medical suite usually includes at least two clinical treatment rooms, with one room configured with an imaging system. The first room 122, for example, contains surgical equipment 174 and a patient transport apparatus 178 and other appropriate medical treatment equipment, supplies, and related items. As described earlier, at times, the patient on the medical transport apparatus 178 may have to be moved to a medical imaging system 176. The second room 124 of the multimodality medical suite 120 includes a medical imaging system, for example, a magnetic resonance imaging system (MRI), a computed tomography scanner (CT), positron emission tomography (PET) or other types of medical imaging equipment 176.

For purposes of this application the phrase "clinical treatment room" shall mean a room in the multi-modality suite that is configured to prepare a patient for surgery, tests, imaging, therapy, pre-therapy, medical device attachment, repair, insertion, or similar procedures and treatments as required by an attending physician, with the room equipped with appropriate equipment, devices and supplies necessary for the intended treatment or procedure.

Figures 6, 7:
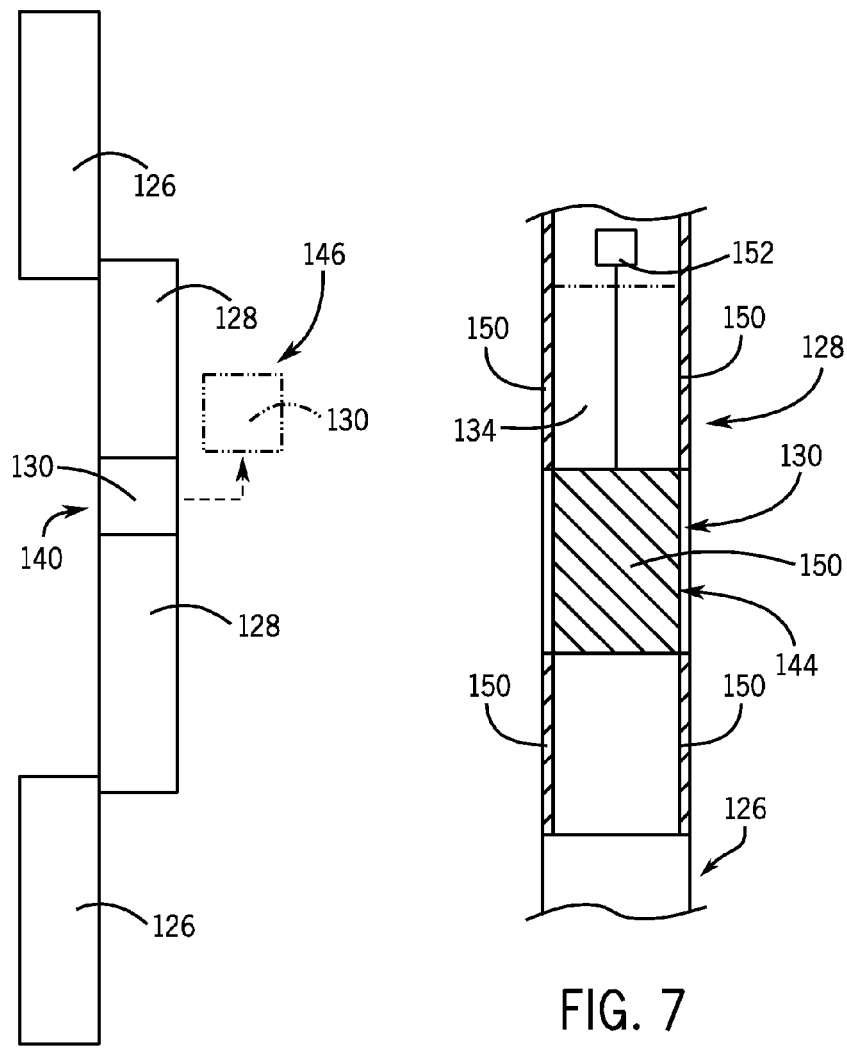
FIG. 6 is a schematic top view of the wall, doors and movable door element illustrated in FIG. 1 and illustrating the movable door element in a second position alongside and substantially parallel to the door.
FIG. 7 is a top detail view of the movable door element illustrated in FIG. 1 in a closed position and coupled to an actuator configured to move the movable door element in and out of a recess defined in the door.

As disclosed and claimed herein, the wall 126 separating the first room 122 and the second room 124 of the multimodality medical suite 120 includes a door 128 which is configured to move and open to allow access between the rooms 122, 124 of the multimodality medical suite 120. FIG. 1 illustrates an example of a pocket door, FIG. 6 illustrates doors that move parallel to the wall 126. The multimodality medical suite 120 includes a flexible raceway 136 which functions as a cable/hose management system which is configured to extend within the length of the multimodality medical suite 120 and selectively extend through a portion 132 of the door 128.

A space 140 is defined in a portion of the door 132. The space 140 is configured to receive one of a movable door element 130 and a shield door component 148 as more fully described below. The movable door element 130 is mounted on the door 128 so that it is automatically displaced by the shield door component 148 coupled to the flexible raceway 136 or moved by an actuator 152 coupled to the movable door element 130.

The movable door element 130 includes a housing 132 which is coupled to the door 128 and configured to selectively move from a first position 144 to a second position 146. The housing 132 is further configured to move to the second position 146 when the shield door component 148, which is coupled to the flexible raceway 136, displaces the housing. The shield door component 148 is then disposed in the space 40 in the portion of the door 132 vacated by the movable door element 130. The housing 132 also includes a shield component 150 disposed in the housing which assists in maintaining the shield integrity of the multimodality medical suite 120.

Figure 5:
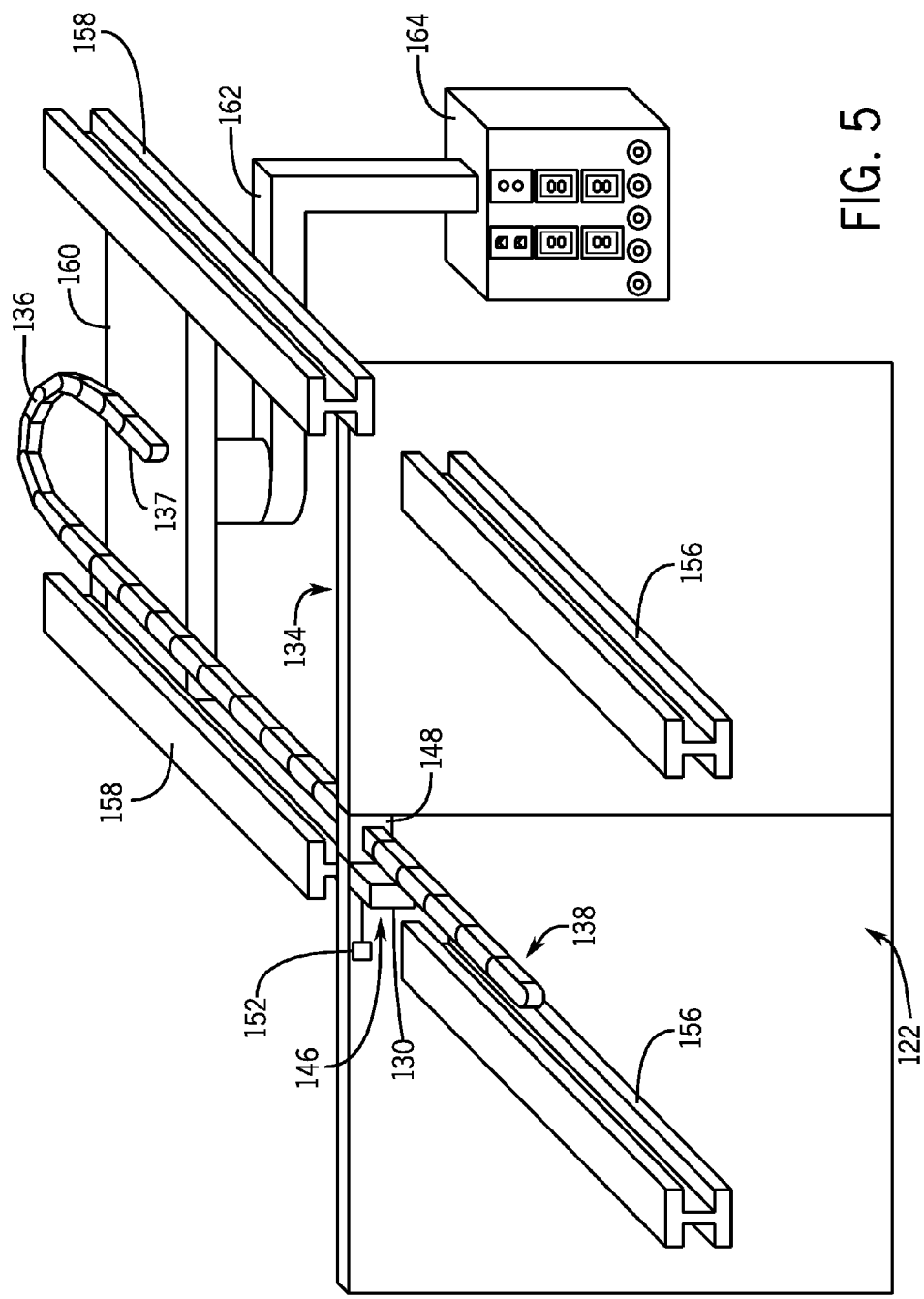
FIG. 5 is a schematic perspective view of the door apparatus of FIG. 1 in a closed position with the support carriage in the second room and the cable/hose management system extending within the first and second rooms of the suite, and the movable door element in a second position at least 90° relative to the door.

The movable door element 130, when in the first position 144 is positioned and functions as a part of the wall 126 of the multimodality medical suite 120. The movable door element, in the second position 146, can be in several different configurations as disclosed herein. In one configuration the movable door element 130, when in the second position, is at least 90 degrees relative to the door 128 (see at least FIG. 5). It is also contemplated that other suitable angles can be established in coordination with the movement of the door element 130, the flexible raceway 136, the door 128, and overall geometry of the multimodality medical suite 120. In another configuration, the movable door element 130 is in a second position that is alongside and substantially parallel to the door 128 (see FIG. 6). In another configuration, the movable door element 130 is configured to move to a second position in a recess 134 defined in one of the wall 126 and door 128 (see FIG. 7).

In some of the above-described configurations, an actuator 152 is coupled to the movable door element 130 and moves the door element 130 from the first to the second position and vice versa. The actuator is one of a spring, a pneumatic cylinder, a hydraulic cylinder, and a motor. A door control controller 172, in some configurations of the movable door element 130, is coupled to the actuator 152 to provide control commands to control the movement of the movable door element 130. In some configurations of the movable door element, the door 128 pushes the movable door element 130 into the recess 134 and an actuator moves the movable door element 130 out of the recess 134.

In an embodiment, the actuator 152 moves the movable door element 130 from the first position 144 in response to the proximity of the shield door component 148. The proximity or distance between the shield door component 148 and the movable door element 130 will vary from suite to suite based on the particular geometry of the suite and its components. The proximity distance can be set by an operator with the controller 172 described below. The controller 172 signals the actuator, for example an electric motor, to activate and move the door element 130. In another embodiment appropriately positioned sensors, for example optical or magnetic sensors, in, for example the door element 130 and shield door component, will provide a signal to an actuator to facilitate the movement of the door element 130.

As discussed above, the room volume of the multimodality medical suite 120 that contains the medical imaging equipment 176 must be shielded from various types of influences to properly function. Accordingly, the multimodality medical suite 120 walls typically include a shield component 150 that is selected from a group consisting of a radiation shield, (for example, foamed aluminum), a radiofrequency shield, (for example, a copper mesh), an acoustic shield, (for example, dimensional cork), a gas seal, (for example, appropriate gaskets), and a combination of any two such shield components.

Figure 3:
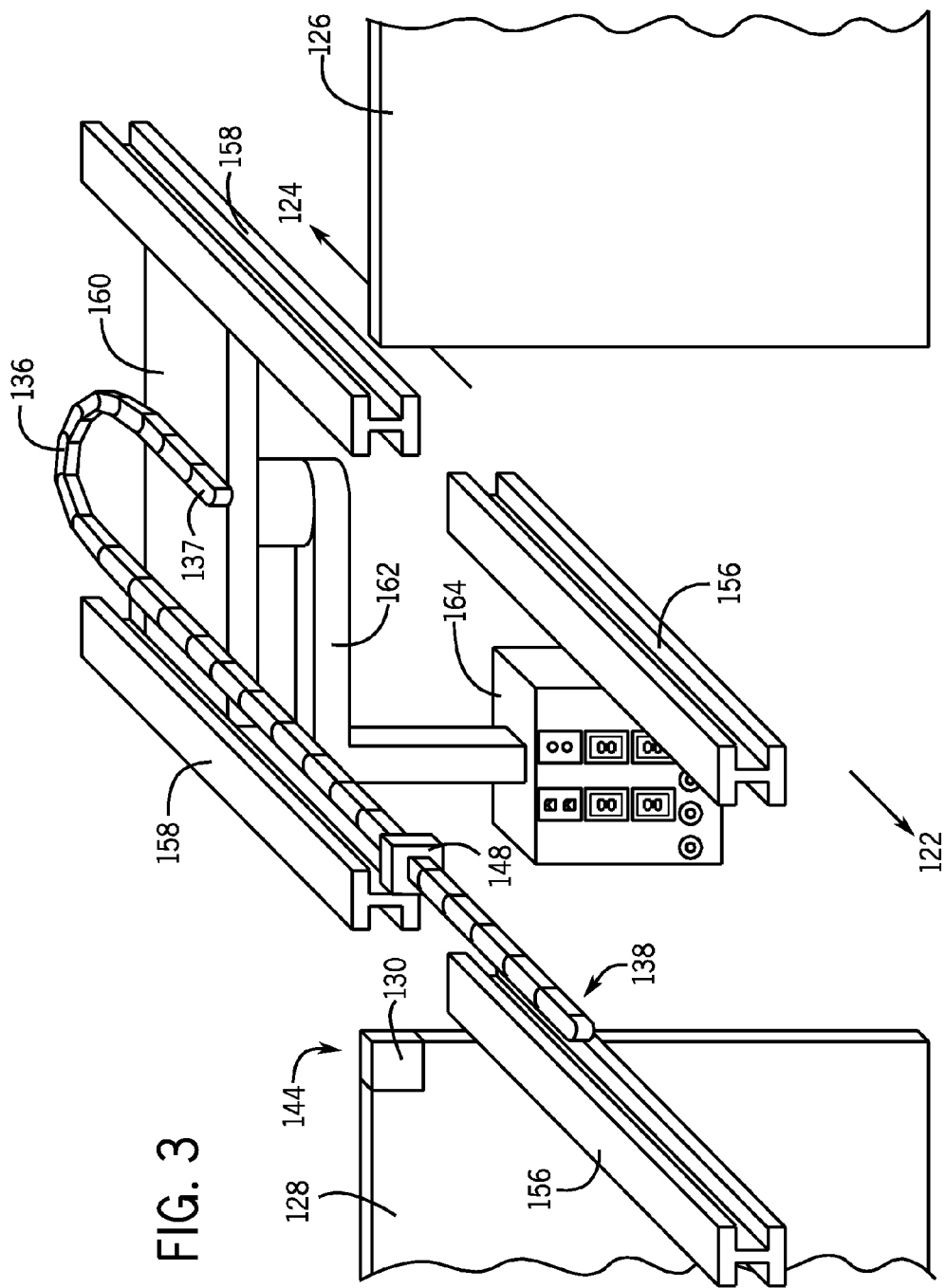
FIG. 3 is a schematic perspective view of the door apparatus of FIG. 1 in an open position with the support carriage and cable/hose management system extending into the second room of the suite.
Figure 4:
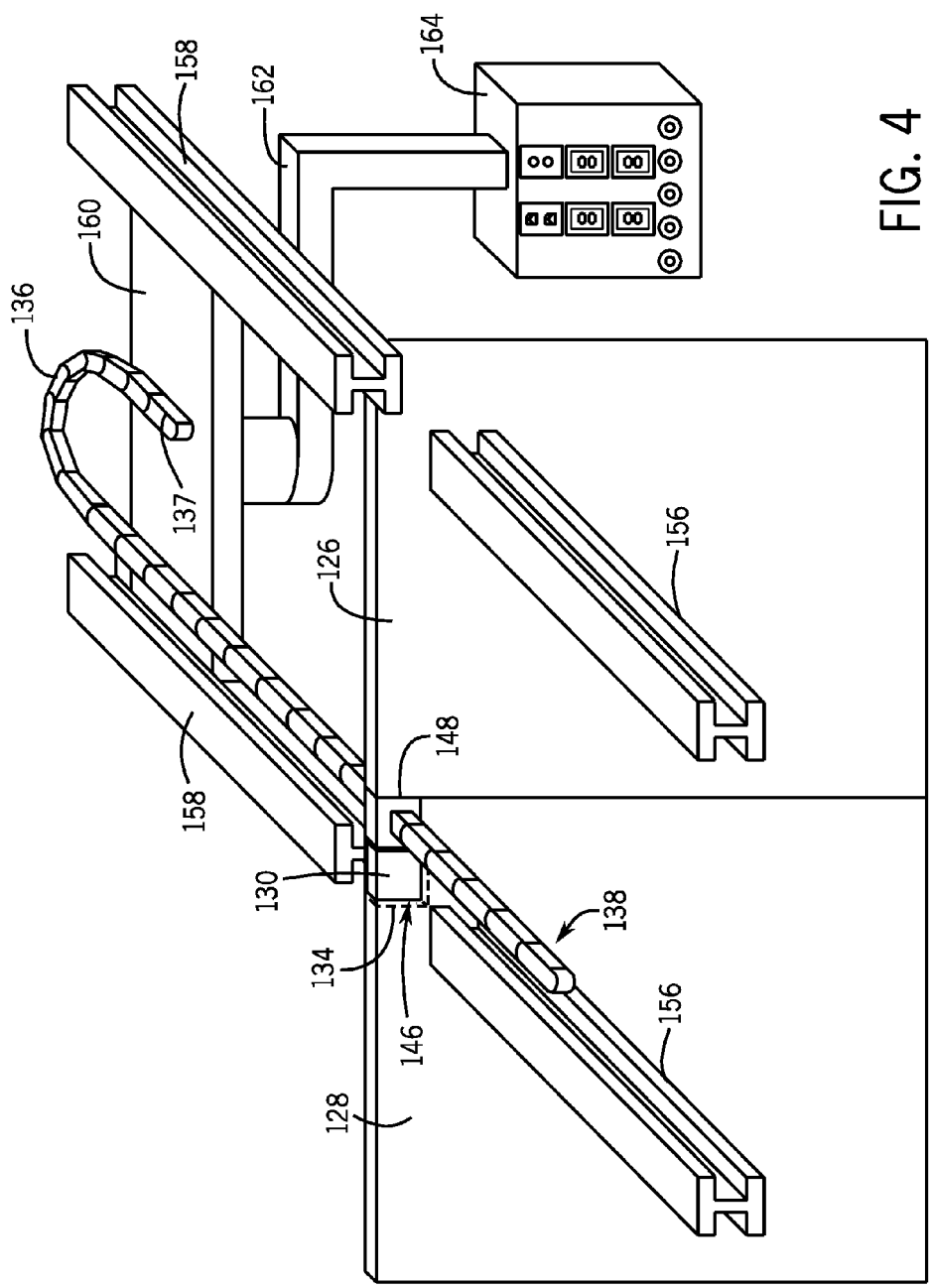
FIG. 4 is a schematic perspective view of the door apparatus of FIG. 1 in a closed position with the support carriage in the second room and the cable/hose management system extending within the first and second rooms of the suite, and the movable door element in a second position in a recess defined in the door.

The movable doors 128 and wall 126 separating the first and second rooms, 122, 124 of the multimodality medical suite 120 must also include a shield component 150. It follows that the movable door element 130 must also provide a shield function and therefore includes a shield component 150 disposed in the housing 142 of the movable door element 130. However, when the patient transport apparatus 178 moves from the first room 122 to the second room 124 including the flexible raceway 136, which passes through the space 140 in the portion of the door 132 (see FIGS. 3-5), shield integrity is compromised unless the shield door component 148 replaces the movable door element which now is in position two 146. The shield door component 148 which is coupled to the flexible raceway 136 provides the necessary shield function when the door 128 is closed and the flexible raceway 136 extends in both the first room 122 and second room 124 as illustrated in at least FIGS. 4 and 5 of this disclosure. As such the shield integrity of the multimodality medical suite 120 is maintained.

The shield door component 148 is positioned along the flexible raceway 136 so that the shield door component 148 either moves the housing from the portion of the door when the flexible raceway 136 is extended between the two rooms 122, 124 of the multimodality medical suite 120 and/or the shield door component 148 is positioned in the space 140 in the portion of the door 142 vacated by the movable door element 130 when the movable door element moves to its second position 146. As described above, the movement of the movable door element 130 from the first position 144 to the second position 146 can be accomplished by actuation of the actuator 152 or the force applied to the movable door element 130 by the door 128.

The multimodality medical suite 120 also includes a track system 154 extending within the first and second rooms 122, 124 of the multimodality medical suite 120. The track system 154 may be positioned in the floor of the multimodality medical suite 120, in the sidewalls of the multimodality medical suite 120, or in the ceiling of the multimodality medical suite 120. As illustrated in the figures, the track system is positioned in or near the ceiling of the multimodality medical suite 120.

In some configurations, the track system 154 may include multiple parts with one part 156 disposed in the first room 122 and a second part 158 of the track system 154 disposed in the second room 124. In the latter configuration, the gap between the track parts 156, 158 is at least the distance equal to the thickness of the door 128 separating the two rooms 122, 124 of the multimodality medical suite 120.

The track system 154 is composed of material, for example metal or composite material, that is sufficiently strong and durable to support any equipment (some of which are described below) coupled to the track system 154. The track system 154 is also compatible and suitable with the medical treatment and medical imaging environment of the multimodality medical suite 120.

A support carriage 160 is coupled to the track system and configured to move between the first and second rooms 122, 124 of the multimodality medical suite 120. One end 137 of the flexible raceway is coupled to the support carriage 160. Another end 138 is coupled to sources of fluid, electric power, and data. The support carriage 160 is further configured to span the gap between the track portions 156, 158 so that motion of the support carriage 160 is not impeded when moving between the first and second rooms 122, 124 of the multimodality medical suite 120.

Figure 10:
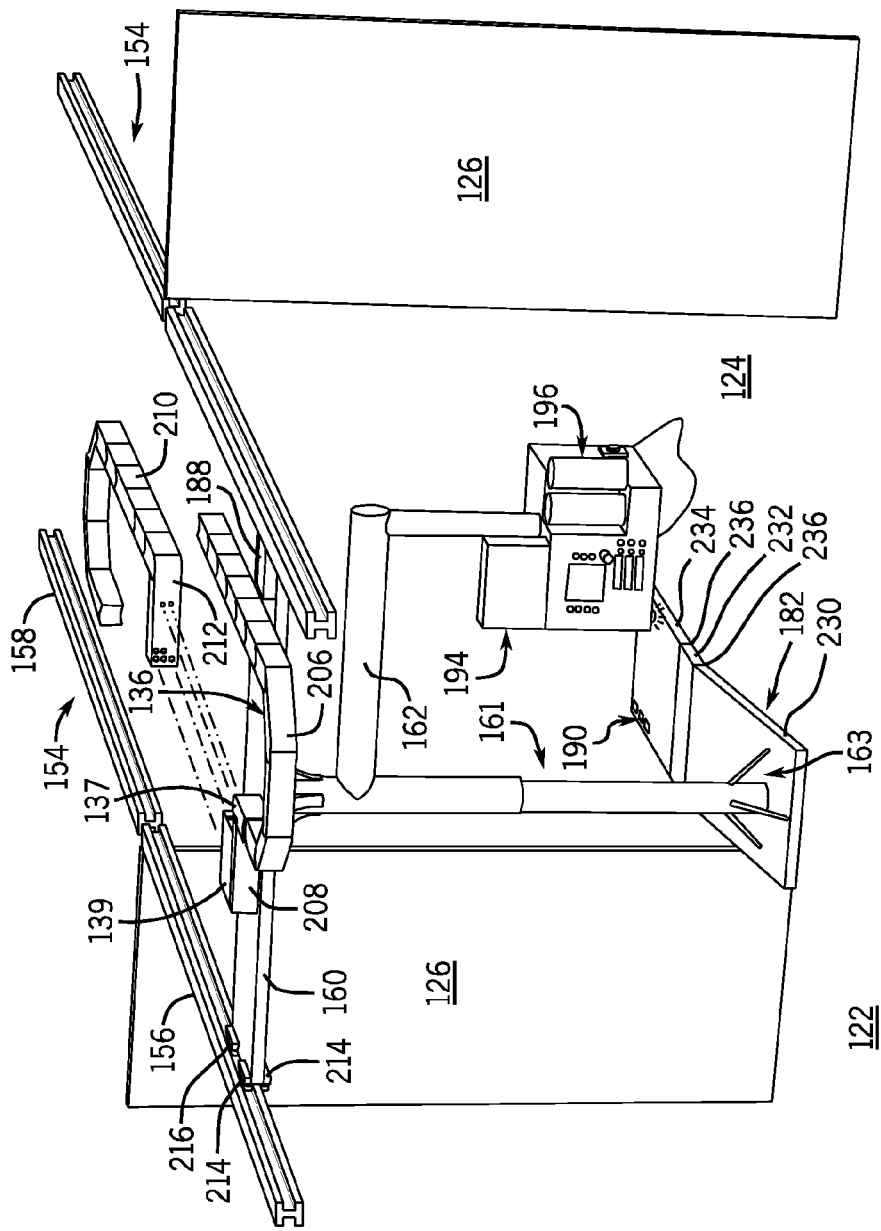
FIG. 10 is a partial perspective view of an exemplary embodiment of a multi-modality medical suite including the patient transport apparatus illustrated in FIG. 8, including a first and second conduit management system configured to couple and decouple with a duplex socket interface module.

In another configuration of a multi-modality medical suite 120, the support carriage 160 includes a duplex socket interface module 139 coupled to the support carriage 160. One end 137 of the flexible raceway 136 is coupled to the duplex socket interface module 139. In FIG. 1 the duplex socket interface module 139 is illustrated having a circular configuration and mounted on a top surface of the support carriage 160. In FIG. 10 the duplex socket interface module 139 is illustrated in a rectangular configuration and also mounted on top of the support carriage 160. However, it should be understood that the duplex socket interface module 139 could also be mounted on a lower surface of the support carriage or integrated into the support carriage interior as determined by a user and/or manufacturer of the patient support transportation system 100 of the multi-modality medical suite 120.

In the above-described configuration of a multi-modality medical suite 120, the flexible raceway includes a first conduit management system 206 and a second conduit management system 210. The first conduit management system 206 includes a first conduit interface module 208 configured to automatically couple with and decouple from the duplex socket interface module 139. The first conduit management system 206 is configured to couple to electrical and data ports in the medical treatment room 122 and to the support carriage 160.

The second conduit management system 210 is coupled to electrical and data ports in the imaging room 124 and includes a second conduit interface module 212 configured to automatically couple with and decouple from the duplex socket interface module 139 upon movement of the support carriage 160 into and out of the medical imaging room 124. The above-described configuration will maintain the integrity of the shielding in the imaging room 124 since the flexible raceway 136, because it is in two parts, does not have to extend through the wall 126 separating the two rooms 122, 124. With this configuration, the patient on the patient bed 182 is still connected to the medical monitoring device 194 and anesthesia delivery system 196 as the patient transport apparatus 178 moves between the two rooms 122, 124.

The support carriage 160 can be articulated by a motor 186, for example an electric motor, or manually by medical personnel. The support carriage 160 is provided with appropriate motive support devices, for example wheels 214, 216 or slats with a slippery surface, configured to smoothly and efficiently allow the support carriage 160 to move along each track of the track system 154, including spanning a gap in the track system 154 if necessary. The support carriage 160 and track system 154 are appropriately grounded electrically to prevent sparking or electrical discharge as a result of movement of the support carriage 160. A motor controller 188, coupled to the motor 186 controls movement of the support carriage 160 as determined by an operator either in the medical suite 120 or remotely.

Figure 2:
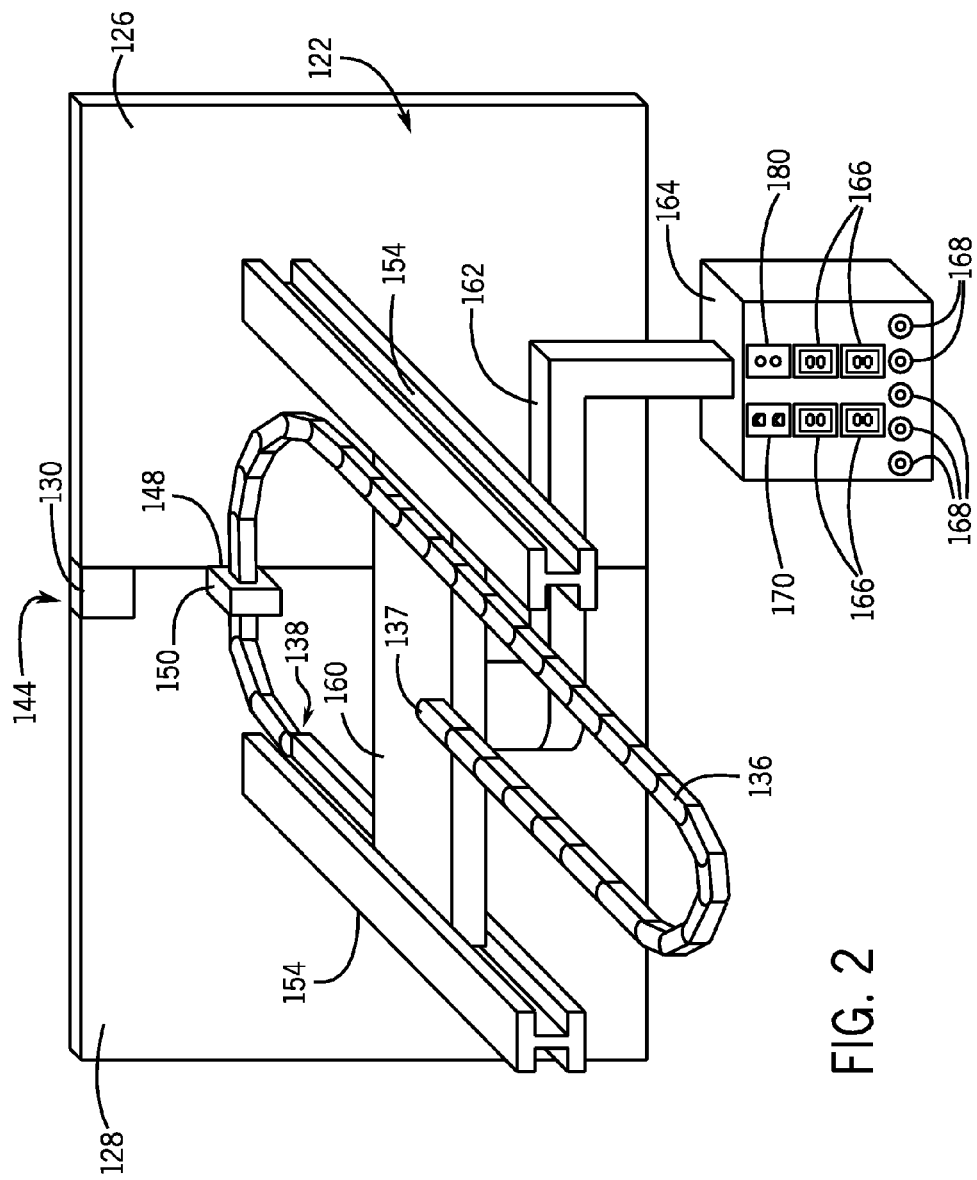
FIG. 2 is a schematic perspective view of the door element of FIG. 1 in a closed (first position) position in the wall between the first and second rooms of the suite, and the support carriage and cable/hose management system all within the first room of the suite.

Coupled to the support carriage 160 is a medical equipment boom 162 which is also coupled to the flexible raceway 136 and configured to move between the first and second rooms 122, 124 of the multimodality medical suite 120 with the support carriage 160. In one embodiment, a medical equipment interface console 164 is coupled to the medical equipment boom 162 with the medical equipment interface console 164 (see FIG. 2) further coupled to electrical 166, fluid 168, and data 170 conduits disposed in the flexible raceway. A suite interface 220, located in at least one of the rooms 122, 124 of the multi-modality suite 120 includes ports for power, fluid, data, video, etc. corresponding to the conduits in the raceways and the ports in the medical equipment interface console 164.

The medical equipment boom 162 is composed of material, for example metal or composite material, that is sufficiently strong and durable to support any equipment, such as the medical equipment interface console 164. The boom, typically is tubular in cross-section and of sufficient volume to accommodate the various above described conduits disposed within the boom.

The boom 162 is of sufficient length to provide movement and position of the console 164 completely around the patient transport apparatus 178. The movement of the boom 162 may be facilitated by a motor, for example an electric motor, but more typically by a manually applied force.

In another embodiment, the support carriage 160 includes a vertical support member 161 which is coupled to the support carriage 160. The vertical support member 161 can be configured to be selectively, vertically adjustable relative to the support carriage 160. As illustrated in FIG. 10, the vertical support member 161 is configured as a telescopic assembly having at least two members. However, it is contemplated that any number of telescopic members can compose the vertical support member as determined by a user and/or manufacturer.

The movement of the vertical support member 161 can be facilitated by an actuator, such as an electric motor, or hydraulic cylinder.

The patient support and transport system 100 also includes a support assembly 184 which is coupled to the vertical support member 161 and configured to selectively articulate a patient bed 182 attached to the support assembly 184. The support assembly 184 for the patient bed 182 is configured to articulate the bed to at least a Trendelenburg, reverse Trendelenburg, tilt, and roll position with appropriate actuators and breaks 236 in the bed 182 and support assembly 184 to angulate and position a patient's legs and torso. The bed 182 typically includes several portions as illustrated in FIG. 10 for example. The portion 230, 232, and 234 are configured to support different portions of a patient in different positions. At least one bed portion, for example 234, also includes attachment sockets 190 described below.

Figure 11:
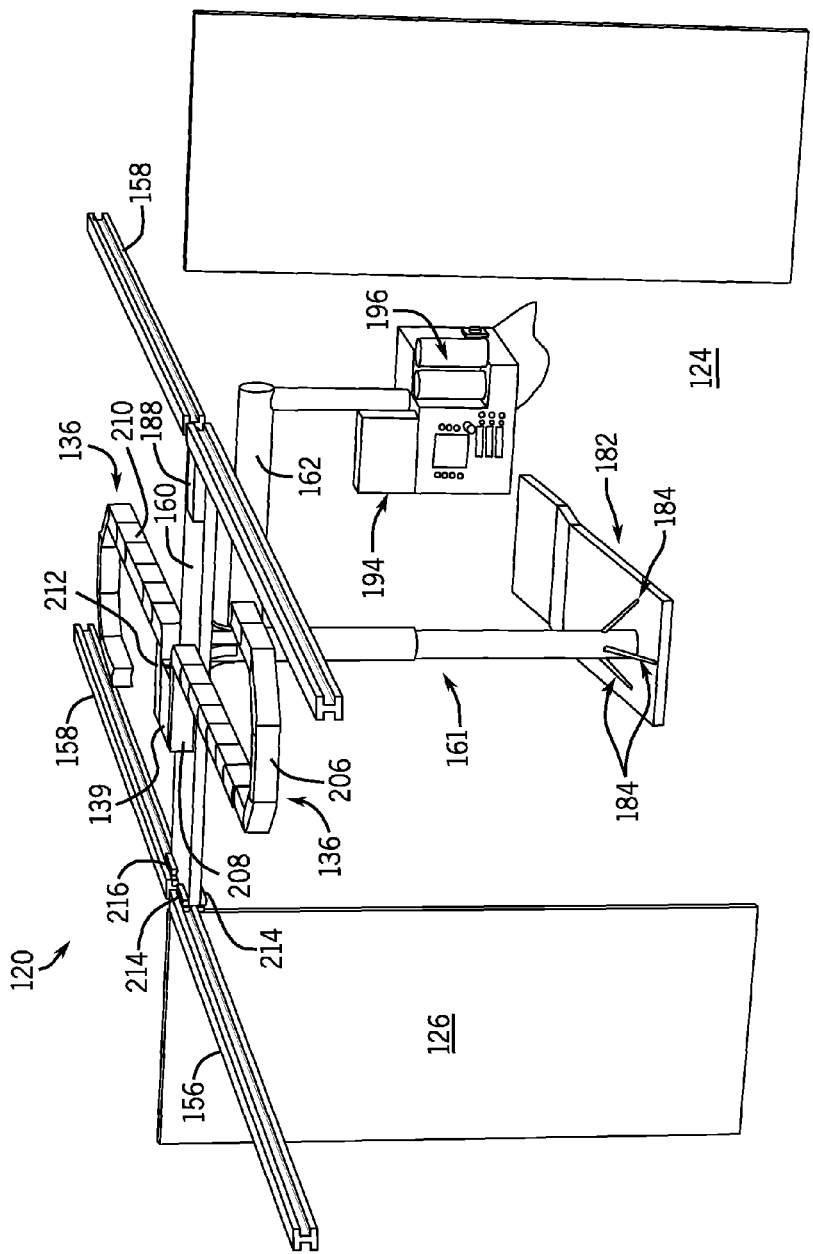
FIG. 11 is a partial perspective view of the medical suite illustrated in FIG. 10, with the patient transport apparatus at a mid-way location between rooms of the multi-modality suite and illustrating both conduit management systems coupled together through the duplex socket interface module for providing a continuous supply of anesthesia gas to the equipment.
Figure 12:
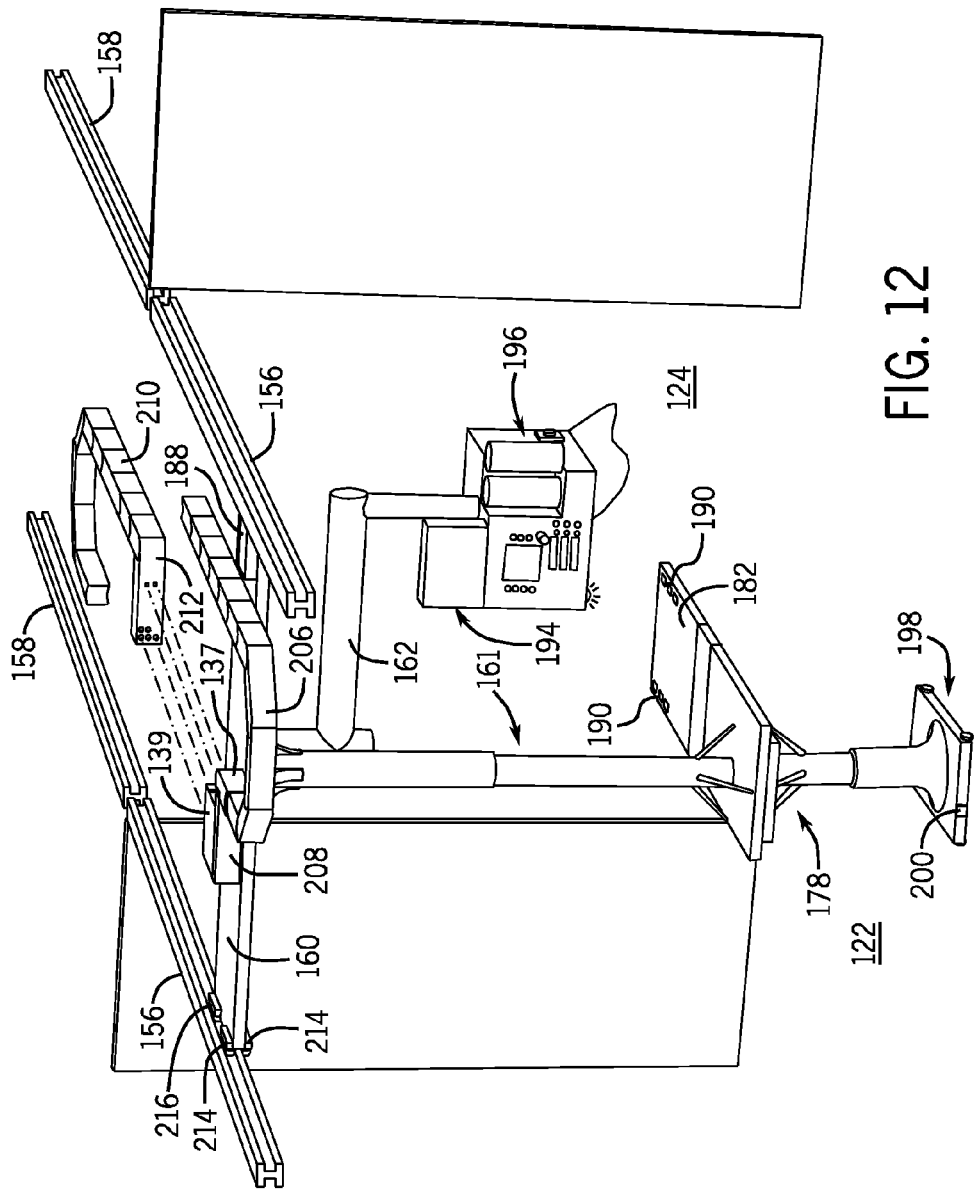
FIG. 12 is a partial perspective view of an exemplary embodiment of a multi-modality medical suite including the patient transport apparatus illustrated in FIG. 10 including an auxiliary support cart coupled to the cantilevered support assembly.
Figure 14:
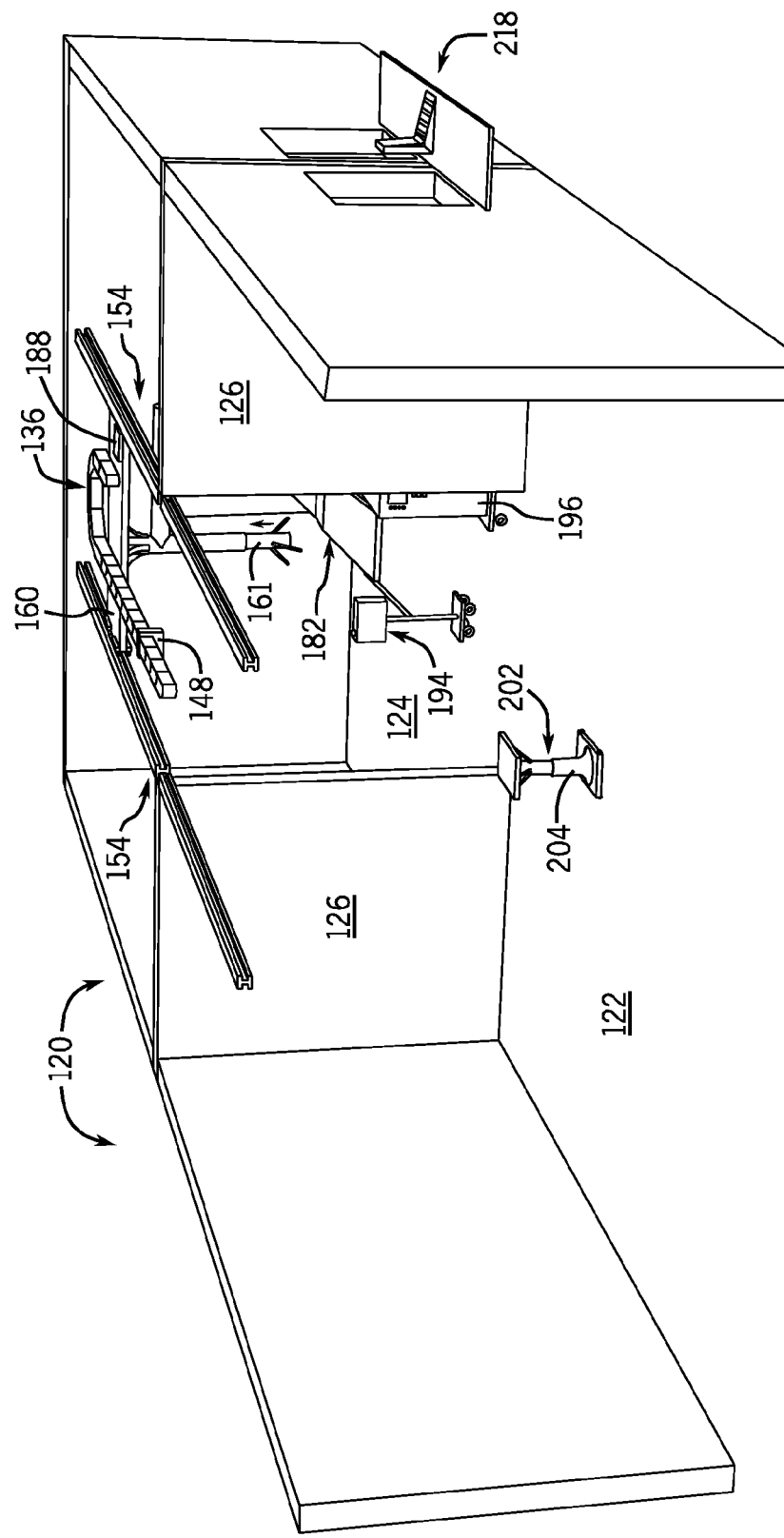
FIG. 14 is a perspective view of the medical suite of FIG. 1, illustrating the decoupled vertical support member and the patient bed in the imaging room of the medical suite.
Figure 15:
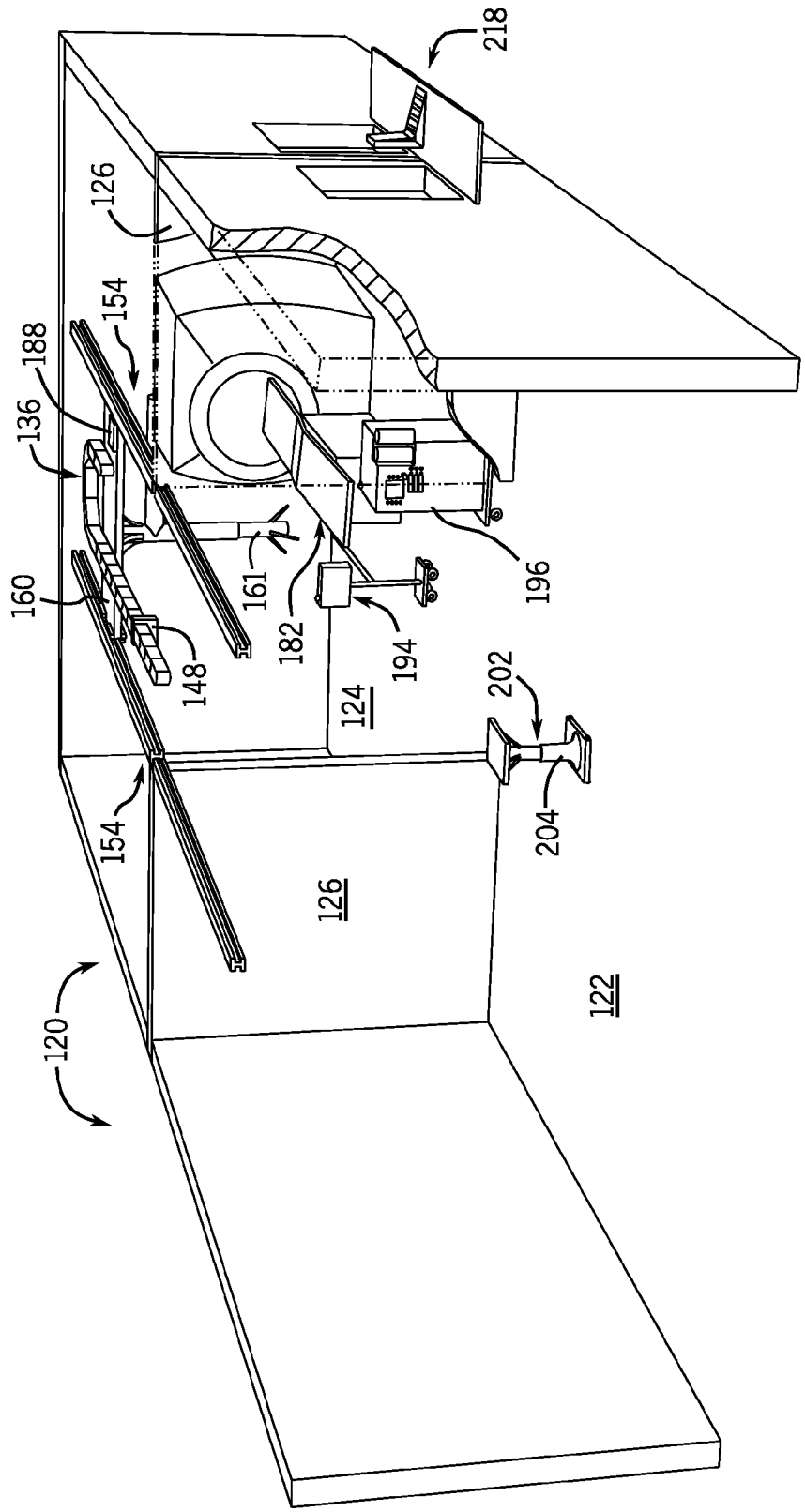
FIG. 15 is a perspective view of the medical suite of FIG. 14, illustrating the patient bed decoupled from the vertical support member and support assembly, with the patient bed on a platform associated with the imaging system.

The support assembly 184 is coupled to the vertical support member 161 in a cantilevered aspect at one end of the support assembly 163 and in one embodiment configured to position a portion of the patient bed 182 at the isocenter of the imaging system 176. See at least FIGS. 10 and 11. In one embodiment, the Patient Transport Apparatus (PTA) 178 is configured to selectively decouple the support assembly 184 and position the patient bed 182 on a platform associated with the imaging system 187. (See at least FIGS. 14 and 15.) The support assembly 163 is coupled to the vertical support member 161 in any convenient and conventional manner that is sufficient to support the patient bed 182 and actuators used to articulate the patient bed.

In another embodiment, the support assembly 184 defines attachment sockets 190, with the attachment sockets 190 configured to receive imaging devices and related attachments. In some circumstances, the imaging system uses accessories that are attached to the support assembly 184 at the sockets 190 to provide, including, power, data signals, patient stabilization, MR surface coils, RF ablation probes, microwave ablation probes, catheter and cryotherapy probes.

In an exemplary embodiment of the medical equipment interface console 164, the medical equipment interface console 164 includes electrical sockets 166, fluid sockets 168, data ports 170, and video ports 180. Each of these ports are coupled to appropriate electrical, fluid, and data conduits disposed in the flexible raceway. Such conduits can be convenient and conventional conduits such as wires, optical paths, hoses, cables, and in some cases wireless communication devices. All the conduits are coupled to appropriate sources and supplies at the end of the flexible raceway 138 coupled to the support carriage 160.

The electric supply is AC and DC power to operate various medical equipment, for example, ventilator, infusion pump, stimulators and monitors, needed for a specific patient on the patient transport apparatus 178. The fluid supply is one of liquid and gas. The liquid can be intravenous fluid and medications. The gas is anesthesia gases such as oxygen, nitrogen, nitrous oxide and such other gases determined by an anesthesiologist. The data signals are from various sensors coupled to a patient and equipment associated with the patient on the patient transport apparatus 178.

In one embodiment the medical monitoring device 194, anesthesia delivery system 196 and interface console 164 are coupled to the equipment boom 162 and connected to the appropriate conduits disposed in the flexible raceway 136 and coupled to the PTA 178. The PTA 178 is also coupled to the support carriage 160. The interface console 164 supplies the electrical power, fluid and gasses for the medical monitoring device 194 and anesthesia delivery system 196.

The patient transport apparatus 178 (PTA) is coupled to the support carriage 160 and may include wheels that can be selectively removed and/or retracted. In another embodiment the PTA 178 is coupled to the support carriage 160 but is not removable.

The PTA is configured to support a patient during medical treatment and in some circumstances during medical imaging. The support of the patient can be provided by, for example, a mattress, a sling system, a system of padded slats, and combinations of such support elements. Some medical imaging procedures require the patient to be transferred to a platform associated with the imaging equipment, for example some MRI machines, however the PTA in one embodiment is configured to keep the patient on the patient bed 182 while the patient is in the suite 120.

The PTA is also configured to support medical equipment, for example intravenous fluid stanchions, cardiac monitoring equipment, and the like. It is contemplated that the PTA 178 in the multimodality medical suite 120 has all monitoring, support, fluid transfer and power provided by the interface console 164 coupled to the boom 162. The PTA is composed of material that is of sufficient strength, durability, and compatibility with the medical equipment of the multimodality medical suite 120, for example stainless steel, or composite materials, for example, an engineered plastic or carbon fiber.

Figure 8:
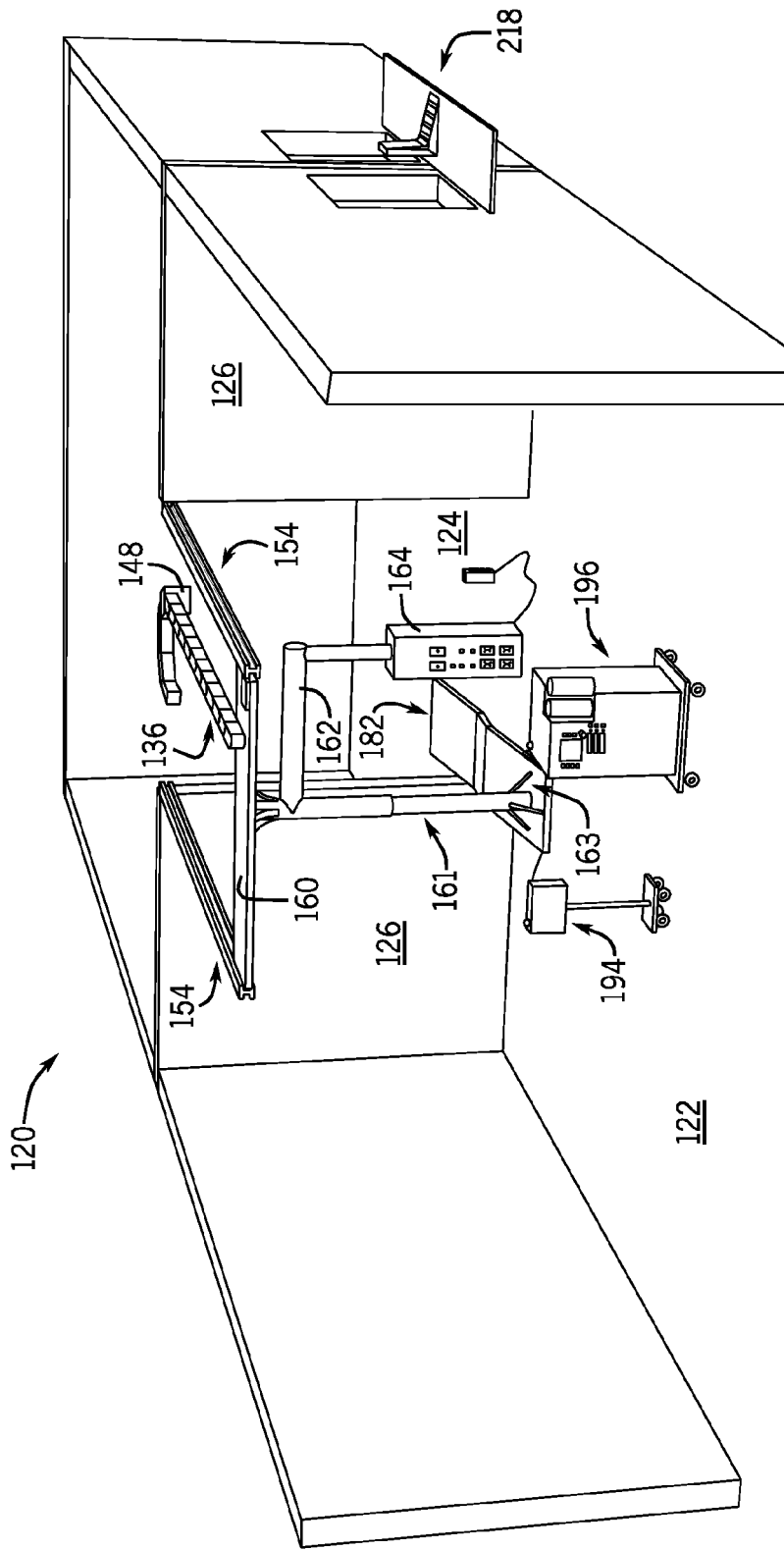
FIG. 8 is a partial perspective view of an exemplary embodiment of a multi-modality medical suite including a patient transport apparatus including a vertical support member coupled to a support carriage and a cantilevered support assembly.
Figure 9:
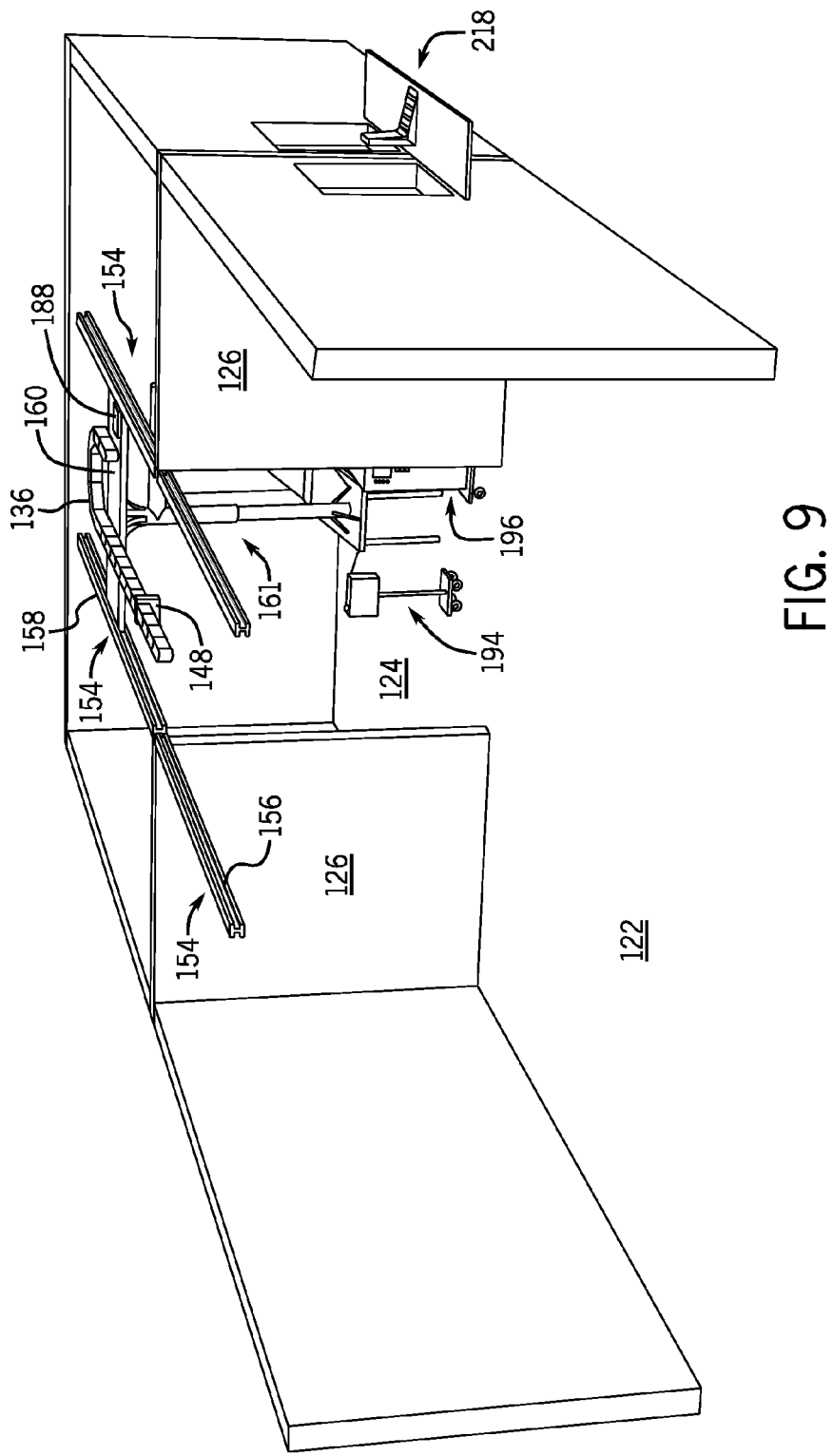
FIG. 9 is a partial perspective view of the medical suite illustrated in FIG. 8, with the patient transport apparatus in a medical imaging room of the medical suite.
Figure 13:
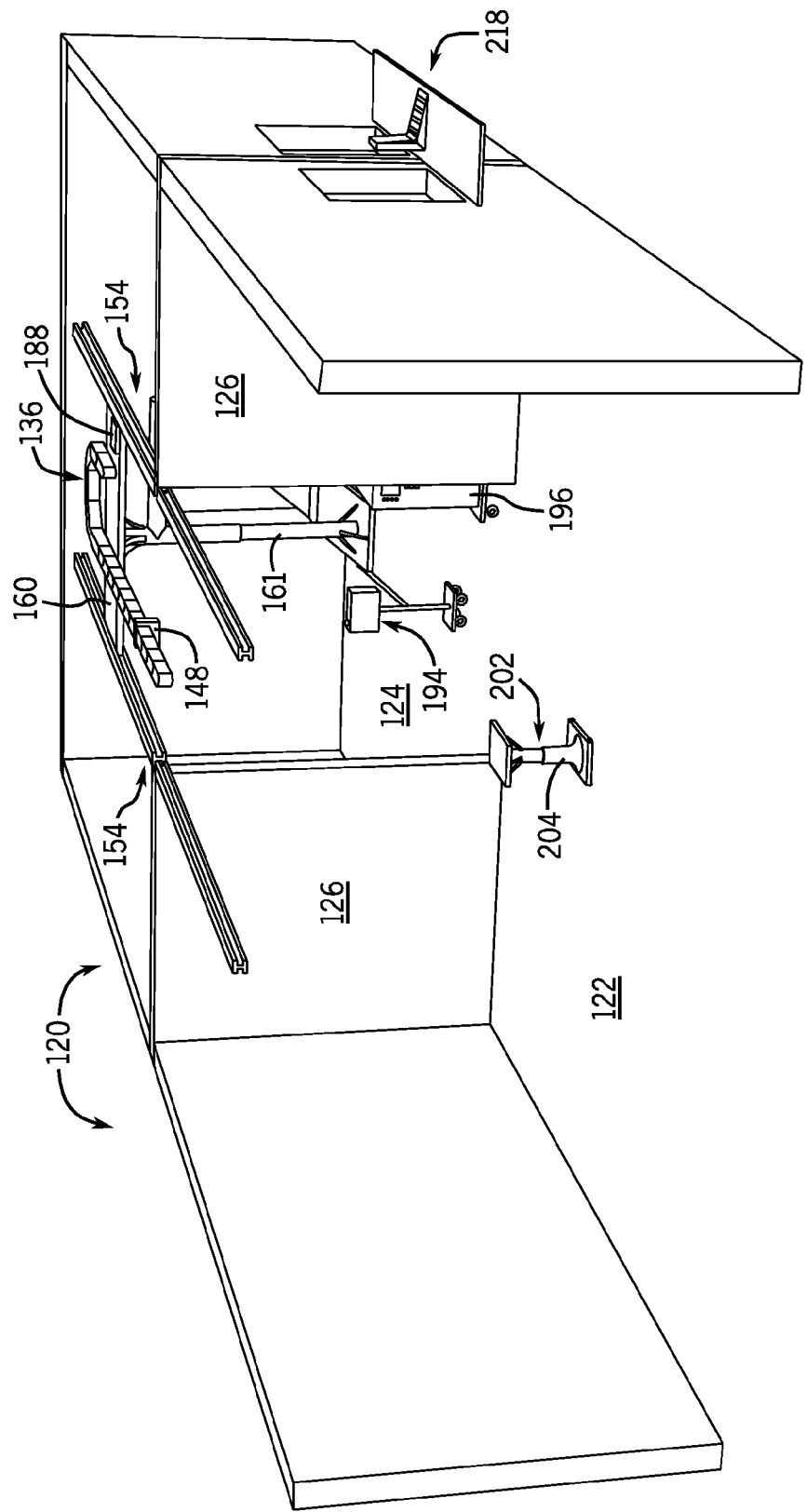
FIG. 13 is a partial perspective view of an exemplary embodiment of a multi-modality medical suite including a fixed support pedestal in a medical treatment room of the medical suite and illustrating the support assembly and patient bed decoupled from the fixed support pedestal and in the medical imaging room of the medical suite.

In one embodiment, the medical equipment is removably coupled directly to the PTA 178 and moves with the PTA as illustrated in FIGS. 8, 9, and 13. The interface console 164 coupled to the equipment boom 162 and connected to the appropriate conduits disposed in the flexible raceway 136 is coupled to the PTA 178. The PTA 178 is also coupled to the support carriage 160. The interface console 164 supplies the electrical power, fluid and gasses for the medical monitoring device 194 and anesthesia delivery system 196. It is also contemplated that the devices 194 and 196 can be independently moved as determined by an operator.

The interface console 164 and the boom 162 will move with the PTA 178 so that a patient on the PTA will still be provided with the necessary monitoring, treatment and related support apparatus. The interface console 164 is configured to be coupled to electrical, fluid and data conduits available in either the first or second rooms, 122, 124.

In another embodiment, the patient support and transport system 100 includes a wheeled auxiliary support cart 198 that is coupled to the support assembly 184. The wheeled auxiliary support cart 198 is configured to move with the PTA 178 in unison with the support carriage 160 as the PTA 178 moves between rooms 122, 124 of the medical suite 120. A motor 200 in the wheeled auxiliary support cart 198 is configured to provide motive force to the wheeled support cart 198 and is also configured to operate a selective, adjustable vertical column which is a part of the wheeled auxiliary support cart 198.

In another embodiment, a fixed port pedestal 202 is included in the patient support and transport apparatus 100. The fixed support pedestal 202 is fixed in the medical treatment room 122 of the multi-modality medical suite 120. The fixed support pedestal 202 is configured for selective, adjustable vertical movement to accommodate various conditions within the medical treatment room 122 and is powered by a motor 204 in the pedestal of the fixed support pedestal 202. The motor, or actuator 204, is also configured to selectively articulate the patient bed 182.

Control of either the wheeled auxiliary support cart 198 and the fixed support pedestal 202 can be controlled locally at each device, or from the medical suite control station 218 typically located outside of the medical suite 120. The medical suite control station 218 is configured to control the various apparatus, lighting, ventilation, positioning, and related operations to coordinate and assist in the functionality of the medical suite 120. Such operations can be controlled with hardwire or wireless connectivity and it is also contemplated that some or all of the functions in the medical suite 120 can be controlled remotely from a location other than within the medical suite 120 or from the medical suite control station 218.

A door control controller 172, in an exemplary embodiment of the movable door element 130, is coupled to the door 128 of the multimodality medical suite 120 and the housing 142. The door control controller 172 is configured to detect the position of the support carriage 160 wherein the controller will cause the actuator 152 to move the housing 142 to the second position 146 when the support carriage 160 moves to the second room 124 and extending the flexible raceway through the space 140 in the portion of the door 162 configured before such operation. The door controller 172 is also coupled to sensors, for example proximity sensors, to prevent the PTA 178 from contacting the door 128 when the door is closed. The door control controller 172 can be mounted directly on the support carriage 160 as illustrated in FIG. 1 or it may be mounted at any convenient location within or without the multimodality medical suite 120.

The controller 172 may be a microprocessor coupled to the various apparatus of the system. The controller 172 may also be a server coupled to an array of peripherals or a desktop computer, or a laptop computer, or a smart-phone. It is also contemplated that the controller is configured to control each individual machine and may be remote from any of the apparatus. Communication between the controller 172 and the various apparatus may be either by hardwire or wireless devices. A memory/data base coupled to the controller may be remote from the controller 172. The controller 172 typically includes an input device, for example a mouse, or a keyboard, and a display device, for example a monitor screen or a smart phone. Such devices can be hardwired to the controller or connected wirelessly with appropriate software, firmware, and hardware. The display device may also include a printer coupled to the controller 172. The display device may be configured to mail or fax reports as determined by a user. The controller 172 may be coupled to a network, for example, a local area network or a wide area network, which can be one of a hardwire network and a wireless network, for example a Bluetooth network or internet network, for example, by a WIFI connection or "cloud" connection.

For purposes of this disclosure, the term "coupled" means the joining of two components (electrical or mechanical) directly or indirectly to one another. Such joining may be stationary in nature or moveable in nature. Such joining may be achieved with the two components (electrical or mechanical) and any additional intermediate members being integrally formed as a single unitary body with one another or the two components and any additional member being attached to one another. Such adjoining may be permanent in nature or alternatively be removable or releasable in nature.

Although the foregoing description of the present shielded, movable door element of a medical imaging/treatment suite and a patient support and transport system has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the shielded, movable door element and patient support and transport system of a medical imaging/treatment suite as described herein may be made, none of which depart from the spirit or scope of the present disclosure. The particular embodiments and applications were chosen and described to provide the best illustration of the principles of the disclosure and its practical application to thereby enable one of ordinary skill in the art to utilize the disclosure in various embodiments and with various modifications as are suited to the particular use contemplated. All such changes, modifications, variations, and alterations should therefore be seen as being within the scope of the present disclosure as determined by the appended claims when interpreted in accordance with the breadth to which they are fairly, legally, and equitably entitled.

What is claimed is:

1. A patient support and transport system for a multimodality medical suite including at least two clinical treatment rooms separated by a wall including a movable door, with at least one room configured with an imaging system, the patient support and transport system comprising:
   a track system comprising a pair of tracks, with one track in one room aligned with another track in the other room;
   a support carriage coupled to the track system and configured to move between the two rooms of the suite;
   a flexible raceway configured to extend within the length of the two rooms of the suite, with one end of the raceway coupled to a duplex socket interface module coupled to the support carriage;
   a vertical support member coupled to the support carriage; and
   a support assembly removably coupled to the vertical support member and configured to one of selectively articulate a patient bed attached to the support assembly and selectively decouple the patient bed wherein the patient bed is positioned on a platform associated with the imaging system.

2. The patient support and transport system for a multimodality medical suite of claim 1, further comprising a motor controller coupled to a motor in the support carriage and configured to control movement of the carriage in a smooth motion from one room to the other room of the suite, with the motor configured to move the support carriage along the track system in response to a signal from the motor controller.

3. The patient support and transport system for a multimodality medical suite of claim 1, wherein the support assembly is coupled to the vertical support member in a cantilevered aspect at one end of the support assembly and configured to position a portion of the patient bed at the isocenter of the imaging system.

4. The patient support and transport system for a multimodality medical suite of claim 1, further comprising attachment sockets defined in the support assembly, with the attachment sockets configured to receive imaging devices.

5. The patient support and transport system for a multimodality medical suite of claim 1, including a medical equipment boom coupled to the vertical support member and coupled to electrical, fluid, and data conduits disposed in the flexible raceway.

6. The patient support and transport system for a multimodality medical suite of claim 5, including a medical equipment interface console attached to the medical equipment boom and coupled to the conduits disposed in the flexible raceway.

7. The patient support and transport system for a multimodality medical suite of claim 5, including a medical monitoring device coupled to the medical equipment boom.

8. The patient support and transport system for a multi-modality medical suite of claim 5, including an anesthesia delivery system coupled to the medical equipment boom.

9. The patient support and transport system for a multi-modality medical suite of claim 1, wherein the vertical support member is selectively, vertically adjustable relative to the support carriage.

10. The patient support and transport system for a multi-modality medical suite of claim 1, including a wheeled auxiliary support cart configured to selectively couple to the support assembly and patient bed.

11. The patient support and transport system for a multi-modality medical suite of claim 10, wherein the wheeled auxiliary support cart includes a motor coupled to cart wheels and configured to move the cart.

12. The patient support and transport system for a multi-modality medical suite of claim 1, including a fixed support pedestal in the medical treatment room configured to selectively engage and support the patient bed, with the fixed support pedestal including an actuator configured to selectively articulate the patient bed.

13. The patient support and transport system for a multi-modality medical suite of claim 1, wherein the flexible raceway comprises:

a first conduit management system including a first conduit interface module configured to automatically couple with and decouple from the duplex socket interface module, with the first conduit management system coupled to electrical and data ports in the medical treatment room; and a second conduit management system coupled to electrical and data ports in the room with the imaging system and including a second conduit interface module configured to automatically couple with and decouple from the duplex socket interface module upon movement of the support carriage respectively into and out of the room with the imaging system.

14. The patient support and transport system for a multi-modality medical suite of claim 13, wherein each of the first and second conduit management systems are configured to function independently when not coupled together.

15. The patient support and transport system for a multi-modality medical suite of claim 1, further comprising a pair of wheel sets mounted on each end of the support carriage, with each wheel set configured to movably engage one of the tracks of the track system and one of each wheel set on each end of the carriage further configured to support the carriage during transition of the carriage from one room to the other room of the multi-modality suite.

* * * * *